(12) United States Patent
Villax et al.

(10) Patent No.: US 6,528,666 B1
(45) Date of Patent: Mar. 4, 2003

(54) PROCESS OF PREPARATION OF FLUMETHASONE 21-ACETATE, OR FLUMETHASONE AND ITS 17-CARBOXYL ANDROSTEN ANALOGUE

(75) Inventors: Ivan Villax, Lisbon (PT); Zita Mendes, Lisbon (PT)

(73) Assignee: Horione Limited (HK)

( * ) Notice: Subject to any disclaimer, the term of this patent is extended or adjusted under 35 U.S.C. 154(b) by 0 days.

(21) Appl. No.: 10/162,862

(22) Filed: Jun. 6, 2002

(30) Foreign Application Priority Data

Dec. 6, 2001 (PT) .................................................. 102628

(51) Int. Cl.⁷ ........................ C07C 50/22; C07D 303/06
(52) U.S. Cl. ....................................... 552/295; 549/544
(58) Field of Search ........................... 552/295; 599/544

(56) References Cited

U.S. PATENT DOCUMENTS 3,499,016 A    3/1970   Lincoln et al.
3,636,010 A    1/1972   Anner et al.

FOREIGN PATENT DOCUMENTS

BA    902292      8/1962
EP    0 610 138   8/1994

*Primary Examiner*—Brian Davis
(74) *Attorney, Agent, or Firm*—Dickstein, Shapiro, Morin & Oshinsky, LLP.

(57) ABSTRACT

A process for the preparation of high purity flumethasone in high yield involves C3 protecting 9,11β-epoxy-17α,21-dihydroxy-16α-methylpregna-1,4-diene-3,20-dione,21-acetate, fluorinating at 6α, removing the C3 protecting group, fluorinating the 9,11-epoxy group. The resulting flumethasone 21-acetate is treated with the methanolic potassium hydroxide in the presence of an oxidation agent, causing a simultaneous hydrolyzation and degradative oxidation, resulting in the formation of 6α,9α-difluoro-11β,17α-dihydroxy-16α-methyl-17β-carboxy-androsta-1,4-diene-3-one in high yield. Flumethasone 21-acetate is alternatively hydrolyzed to yield flumethasone free alcohol.

18 Claims, No Drawings

PROCESS OF PREPARATION OF FLUMETHASONE 21-ACETATE, OR FLUMETHASONE AND ITS 17-CARBOXYL ANDROSTEN ANALOGUE

Flumethasone, 6α,9α-difluoro-16α-methylprednisolone was described for the first time in 1962. Although this corticosteroid has an enhanced antiinflammatory activity its clinical application has not been widely used.

At the present time, its economical preparation on an industrial scale is ever more important because it is also an excellent starting material for the production of new difluoro-17-carboxyl androstenes, which are becoming increasingly important from a clinical point of view.

Flumethasone was patented for the first time in U.S. Pat. No. 3,499,016 (1962) as well as, among other patents, British Patent 902,292 (1970).

The new synthetic techniques developed since 1970 naturally permit a more efficient production of flumethasone with considerably increased yields compared to those obtained with the initial patents.

The present invention relates to a new process for the preparation of flumethasone as well as to the preparation of 6α,9α-difluoro-11β, 17α-dihydroxy-16α-methyl-17β-carboxy-androsta-1,4-diene-3-one which is also called "hydroxyacid", an excellent starting material for the production of fluticasone and other new antiinflammatory compounds of the androsta-1, 4-diene series. The "hydroxyacid" was first described and claimed in U.S. Pat. No. 3,636,010 (priority 1968).

The European Patent 0 610 138 B1 (1994) describes a new synthetic route for the preparation of the so called "hydroxyacid". However, the present invention represents considerable unexpected advantages in relation to this prior process patent, namely:

the reaction sequence is reduced by one reaction step and by the elimination of the desolvatation step of 6α,9α-difluoro-11β,17α-dihydroxy 16α-methyl 17β-methoxycarbonyl androsta-1,4-diene-3-one, an additional production step, the present process avoids the use of a highly toxic reagent, dimethyl sulphate, permits the simultaneous deacetylation and degradative oxidation of the pregnane side chain forming directly the equivalent androstan derivative, increased yield of the hydroxyacid with excellent purity.

Whilst all the reaction steps of the present invention are realised in the pregnane series excepting the last one thus permitting an efficient preparation of flumethasone, the reaction sequence of EP 0 610 138 B1 transforms the common starting material of both processes as from the first step into the androstane series.

According to the present invention the preparation of flumethasone and its 17β-carboxyl androsten analogue follows the following steps:

a) the starting material of the formula:

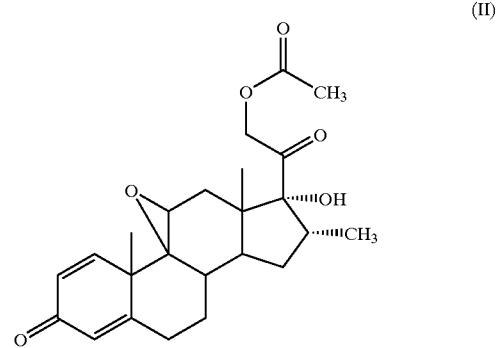

(II)

is reacted with benzoyl chloride so as to obtain the new compound with the following formula:

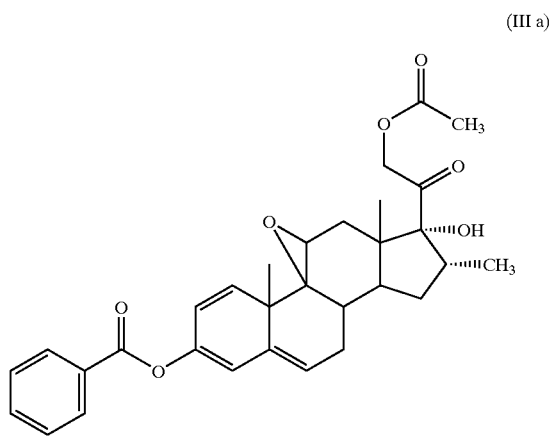

(III a)

b) the benzoate of the formula III a) is then reacted with an electrophilic fluorination agent so as to introduce fluorine in the position C6 yielding the new compound of the formula:

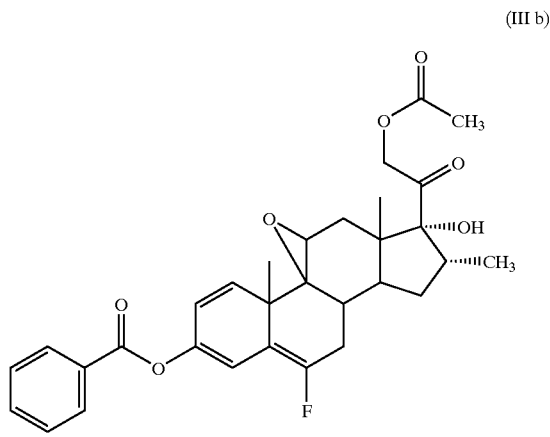

(III b)

c) which yields, after eliminating the protection in C3, a compound of the formula:

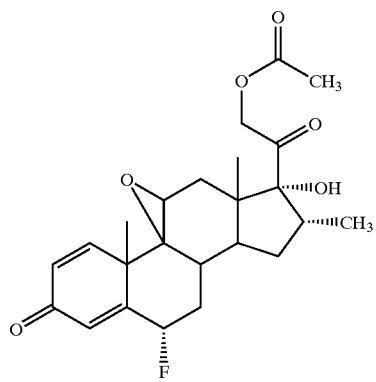

(IV)

d) thereafter the compound IV is reacted with hydrofluoric acid yielding flumethasone 21-acetate of the formula:

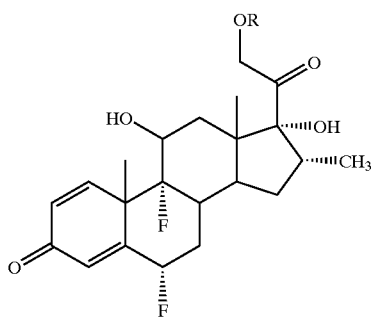

in which R is a residue of acetic acid, that is 6α,9α-difluoro-11β,17α, 21-trihydroxy-16α-methyl-pregna-1,4-diene-3,20-dione,21-acetate;

e1) followed by the hydrolisation of this compound with methanolic potassium hydroxide yielding flumethasone free alcohol, in which R is hydrogen;

e2) alternatively, flumethasone acetate is reacted with methanolic potassium hydroxide and hydrogen peroxide solution yielding the desired compound, so called "hydroxyacid" of the formula:

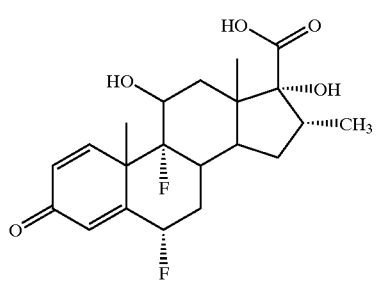

(I)

The present invention permits the direct transformation of flumethasone acetate into compound I.

The compounds III a) and III b) are new.

The compound I can also be obtained as described in U.S. Pat. No. 3,636,010 by oxidizing flumethasone free alcohol.

The starting material of the present process is commercially available and widely used in the preparation of corticosteroids such as dexamethasone and icomethasone.

So as to introduce fluorine in C6 with an electrophilic fluorination agent it is necessary to activate first the position C6. For that purpose the 3-ceto group is enolised by carboxylic acid chloride forming an enolic ester residue of the formula —COR in which R is an aryl or aralkyl group. The preferred compound for the enolisation is benzoyl chloride yielding the compound of formula III a) in the presence of a tertiary amine, like pyridine. The preferred solvent is N,N'-dimethylacetamide and the reaction is realised at a temperature of 80 to 85° C., yielding the Δ3,5 enol benzoate. Thereafter the compound III a) is reacted with an electrophilic fluorination agent to yield the corresponding 6 fluoro derivative. The preferred fluorination agent is the 1-chloromethyl-4-fluoro-1,4-diazoniabicyclo [2.2.2]octane bis(tetrafluoroborate), Selectfluor®. So as to realise the fluorination at C6, the preferred solvent is acetonitrile in presence of water at a temperature of −5° C.±2° C. After the C6 fluorination the 3 enolic ester could be easily transformed into the system of 3-ceto-1,4-diene yielding the compound IV. The elimination of the enolic ester is realised by an aqueous solution of sodium metabisulfite and ammonia.

In the next step a 9,11-epoxy group of compound IV is reacted with a concentrated aqueous solution of hydrofluoric acid or with a solution of hydrogen fluoride in N,N'-dimethylformamide by per se known processes at a temperature inferior to 25° C. When compound IV is practically completely reacted, the reaction mixture is poured into a mixture of ice and ammonia sufficient to neutralise the hydrofluoric acid and precipitate simultaneously the flumethasone 21-acetate with a high yield and purity. Of course the product obtained can be recrystallized for instance from methanol. Also the 21-acetate obtained can be subsequently hydrolized by any of the known processes yielding flumethasone free alcohol. One of the preferred processes is realised in degassed methanolic potassium hydroxide at a temperature comprised between −15° C. and −5° C. End of the reaction is ascertained by HPLC after one hour and it is considered complete when the amount of starting compound is inferior to 1%.

In order to realise the degradative oxidation, according to prior art, flumethasone is suspended in tetrahydrofuran and a solution of the oxidation agent is added dropwise. The substrate first starts to dissolve followed by precipitation. The oxidation is performed preferably at 20° C. employing, for example, periodic acid. After one hour of stirring, completion of the reaction is controlled by HPLC. Once the amount of non-reacted flumethasone is inferior to 0.3%, the reaction is considered complete. Subsequently, the reaction mixture containing compound I is precipitated by adding to an aqueous solution of sodium metabisulfite and ice.

According to the present invention one can deacetylate and oxidise simultaneously flumethasone 21-acetate by methanolic potassium hydroxide and aqueous hydrogen peroxide yielding, after completion of the reaction, the desired hydroxyacid, compound I, by acidifying the reaction mixture with diluted hydrochloric acid until pH 2. This reaction is performed at 10° C., ±2° C. with agitation until the reaction is complete.

The cumulative stoichiometric yield of the process described in EP 0 610 138 B1 so as to obtain unrecrystallized compound I is 48.9% as from 9,11β-epoxy-17α,21-dihydroxy-pregna-1,4-diene-3,20-dione, whilst according to the present process the cumulative stoichiometric yield obtained is 62.4%, as per examples 1 b), 2 and 4, as from the 21-acetate of the above starting material. So as to obtain a valid comparison of yields, the starting material of EP 0 610

138 B1 has been first acetylated with a yield of 110% w/w and the cumulative stoichiometric yield was calculated on basis of this value and of examples 1 b), 2 and 4, resulting in 61.7%.

The following examples serve to illustrate the present invention without limiting its scope.

EXAMPLE 1

9,11β-epoxy-6α-fluor-17α,21-dihydroxy-16α-methyl-pregna-1,4-diene-3,20-dione, 21-acetate (Formula IV)

a) One dissolves in an inert atmosphere 50 g of 9,11α-epoxy-17α, 21-dihydroxy-16α-methyl pregna-1,4-diene-3,20-dione,21-acetate in 25 ml of dimethylacetamide (DMA). One adds 65 ml of pyridine and the reaction mixture is heated with stirring to between 80° C. and 85° C.

Subsequently one adds 33 ml of benzoyl chloride, protected from light, and continues to stir during two to three hours at this temperature and cools it down to 40° C. when the reaction is completed. Subsequently, one adds 75 ml of methanol and continues stirring at 40° C. for another 30 minutes followed by cooling down the reaction mixture to 20–25° C. Subsequently, one adds the reaction mixture to 1,000 ml of water containing 57.5 ml of hydrochloric acid and 100 ml of dichloromethane. After the extraction, one separates the phases and the aqueous phase is again extracted by an additional 100 ml of dichloromethane. Subsequently, the organic phase is washed with water and with an aqueous solution of sodium hydroxide. The dichloromethane solution thus obtained is evaporated in vacuum to dryness yielding an oil, 3-benzoyloxy-9,11β-epoxy-17,21-dihydroxy-16α-methyl-pregna-1,3,5-triene-20-one 21-acetate (Formula III a), which is taken up by 150 ml of acetonitrile cooled down to between −5° C. and 0° C. Subsequently, one adds the solution of enolbenzoate to a suspension of 44.5 g of 1-chloromethyl-4-fluoro-1,4-diazoniabicyclo[2.2.2]octane bis(tetrafluoroborate) Selectfluor®, in 175 ml of acetonitrile containing 5 ml of water.

Once the fluorination reaction is completed at C6 (Formula III b), the reaction mixture is poured into a solution of 100 ml water, 1.2 g of sodium metabisulfite, 5 ml of ammonia 25% and 200 ml of dichloromethane. The pH of the solution is adjusted to between 7–8 and is stirred for 30 minutes after which the phases are separated and the organic phase is washed with ammonia 12.5%. Subsequently, the organic phase is evaporated in vacuum until dryness and substituted by methanol. The desired compound crystallizes, is then filtered and dried at 40 to 45° C., yielding 40 g of the title product with a purity by HPLC of 90%, in area.

b) One repeats Example 1 a), but omitting the extraction of the 3-enol benzoate formed, and adding slowly and directly to the reaction mixture 44.5 g of Selectfluor® crystals in four portions. When the content of the starting material is less than 1%, the reaction mixture is poured into 100 ml of water containing 1.2 g of sodium metabisulfite. The pH is then adjusted to between 7 and 7.5, the solution is stirred for 30 minutes, and the precipitate is filtered and washed. Subsequently, the product thus obtained is washed by suspending it in 150 ml of methanol with stirring. After stirring for 30 minutes, it is filtered and dried at a temperature between 40°–45° C., yielding 46 g of 9,11β-epoxy-6α-fluoro-17α,21-dihydroxy-1,4-diene-3,20-dione,21-acetate with a purity of 91.6%.

EXAMPLE 2

6α,9α-difluoro-11β,17α,21-trihydroxy-16α-methyl-pregna-1,4-diene-3,20-dione,21- acetate (Flumethasone acetate)

36 g of the compound obtained in Example 1) is dissolved in an inert atmosphere in 360 ml of a complex of hydrogen fluoride and dimethylformamide (~64% w/w) at a temperature of 20° C.±30°. After stirring for three hours at this temperature, it is poured, under agitation, into a mixture of 3,000 ml of water, 1,000 ml of ice and 800 ml of ammonia 25% maintaining the temperature below 25° C. during the whole precipitation. One adjusts the pH to between 4.5 to 5 with ammonia and continues the agitation for one more hour. Subsequently, the precipitate is filtered and washed with water until neutral pH. After drying the compound is dissolved in a mixture of 333 ml of dichloromethane and 148 ml of methanol.

The solution is concentrated until one reaches a volume of 89 ml. The desired product crystallizes. After filtration, it is dried at between 40 to 45° C., yielding 29.2 g of 6α,9α-difluoro-11β,17α,21-trihydroxy-16α-methyl-pregna-1,4-diene-3,20-dione,21-acetate with a purity of 95% by HPLC, in area.

EXAMPLE 3

6α,9α-difluoro-11β,17α,21-trihydroxy-16α-methyl-pregna-1,4-diene-3,20-dione (Flumethasone)

1.4 g of potassium hydroxide is dissolved in 140 ml of degassed methanol in an inert atmosphere and the solution is cooled to between 0° C. and −5° C. Subsequently, the solution is added under stirring to a suspension of 28 g of the compound obtained in the previous example, in 700 ml of degassed methanol. It is stirred during 1 to 2 hours at a temperature of −10° C.±2° C. Once the reaction is completed, determined by HPLC, one adds acetic acid until pH 7. Subsequently the volume is reduced under vacuum to ~224 ml. Then it is cooled to 10° C. and 140 ml of cold water is added. After stirring for one hour at a temperature of between 5° C. to 10° C., the compound is filtered, washed with water and dried at 45° C., yielding 22.4 g of the title compound with a purity of 96% by HPLC in area.

EXAMPLE 4

6α,9α-difluoro-11β,7α-dihydroxy-16α-methyl-17β-carboxy-androsta-1,4-diene-3-one (Formula I, "hydroxyacid")

2 g of potassium hydroxide is dissolved in a mixture of 100 ml of methanol and 100 ml of water in an inert atmosphere. Subsequently, one adds 10 ml of an aqueous hydrogen peroxide solution (130 vol.) and then cools the reaction mixture to 10° C.±2° C. and one adds 5 g of flumethasone 21-acetate. One stirs overnight at this temperature and once the reaction is completed one adjusts it to pH 2 with hydrochloric acid. Subsequently, it is filtered and washed with water until neutral pH and dried at 45° C. The yield in the title compound is 80% w/w, corresponding to a stoichiometric yield of 91.3%.

EXAMPLE 5

6α,9α-difluoro-11β,17α-dihydroxy-16α-methyl-17β-carboxy-androsta-1,4-diene-3-one 22 g of flumethasone free alcohol obtained in example 3 is suspended in 110 ml of tetrahydrofuran in an inert atmosphere and is cooled to 20° C.±2° C. 17.6 g of periodic acid in 70 ml of water is slowly added under stirring. After agitation at the same temperature, one controls the end of the reaction by HPLC, which is generally complete after two hours. Subsequently, the reaction mixture is poured into a solution of 33 g of sodium metabisulfite in 770 ml of water and 330 ml of ice. The product precipitates, is filtered and washed with water until a neutral pH and is dried at 40° C. to 45° C., yielding 21 g of the title compound with a purity of 96% in area determined by HPLC.

After recrystallizing the compound thus obtained in ethanol, one obtains 6α,9α-difluoro-11β,17α-dihydroxy-16α-methyl-17β-carboxy-androsta-1,4-diene-3-one in high purity having the following analytical values:

optical rotation=+64.40° (c=1%DMF)

KF −0.09%

Purity by HPLC=99.2% in area

Principal absorption peaks in infrared at 1698 cm$^{-1}$–1660 cm$^{-1}$ and 1614 cm$^{-1}$–1603 cm$^{-1}$.

What is claimed is:

1. A process for preparing flumethasone, 6α,9α-difluoro-11β, 17α,21-trihydroxy-16α-methyl-pregna-1,4-diene-3,20-dione, flumethasone 21-acetate or its 17-carboxyl androsten analogue of the formula:

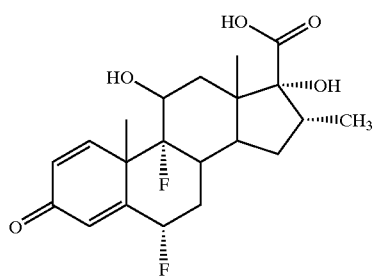
(I)

characterized by the fact that a compound of the formula:

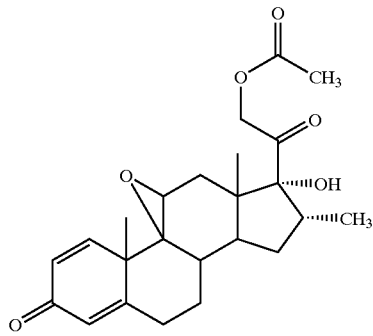
(II)

is reacted with benzoyl chloride to form a 3-enolic ester of the formula:

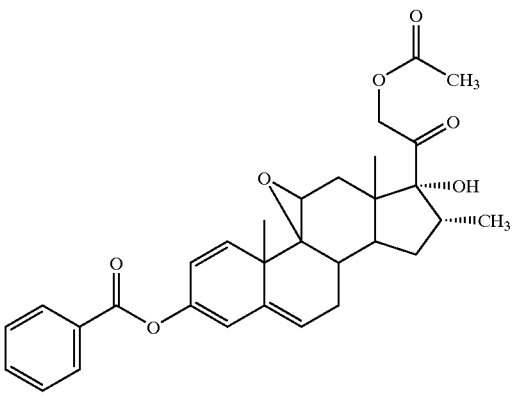
(III a)

the enol benzoate (III a) thus obtained is reacted with an electrophilic fluorination agent so as to introduce fluorine the 6α-position,

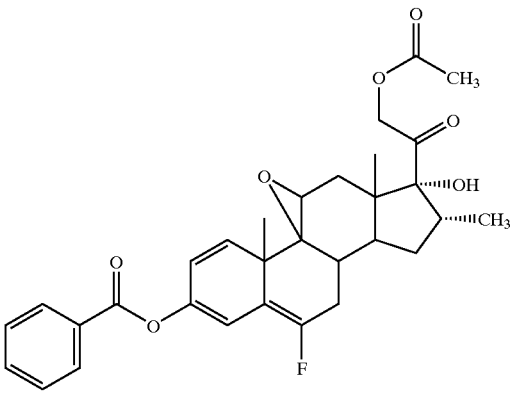
(III b)

the enol benzoate (III b) is deprotected at C3 to yield a compound of the formula:

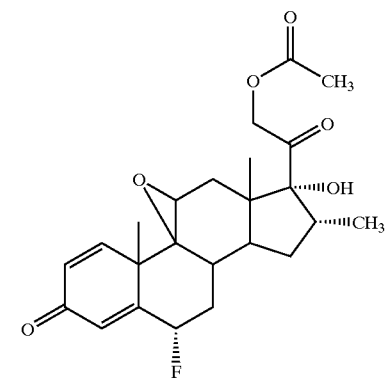
(IV)

the 9,11-epoxy group of compound IV is fluorinated by reaction with hydrofluoric acid to yield flumethasone 21-acetate, and optionally the flumethasone 21-acetate is hydrolyzed in the presence or absence of an oxidization agent to yield compound I or flumethasone, respectively.

2. A process according to claim 1, characterized by the fact that the flumethasone 21-acetate is reacted with methanolic potassium hydroxide in the absence of an oxidization agent to yield flumethasone.

3. A process according to claim 1, characterized by the fact that the flumethasone 21-acetate is reacted with methanolic potassium hydroxide in the presence of an oxidation agent to yield compound I.

4. A process according to claim 3, characterized by the fact that the oxidation agent is aqueous hydrogen peroxide solution.

5. A process according to claim 4, characterized by the fact that the electrophilic fluorination agent is 1-chloromethyl-4-fluoro-1,4-diazoniabicyclo[2.2.2]octane bis(tetrafluoroborate).

6. A process according to claim 5, characterized by the fact that the deprotection in position C3 is carried out using an aqueous solution of metabisulfite and ammonia.

7. A process according to claim 6, characterized by the fact that the reaction medium for the reaction with benzoyl chloride is N,N'-dimethylacetamide and pyridine; and the reaction medium for the reaction with the electrophilic fluorination agent is acetonitrile in the presence of water.

8. A process according to claim 7, characterized by the fact that the reaction temperature for the reaction with benzoyl chloride is +80–85° C.; and the reaction temperature for the reaction with the electrophilic fluorination agent is −5±2° C.

9. A process according to claim 1, characterized by the fact that the electrophilic fluorination agent is 1-chloromethyl-4-fluoro-1,4-diazoniabicyclo[2.2.2]octane bis(tetrafluoroborate).

10. A process according to claim 9, characterized by the fact that the deprotection in position C3 is carried out using an aqueous solution of metabisulfite and ammonia.

11. A process according to claim 10, characterized by the fact that the reaction medium for the reaction with benzoyl chloride is N,N'-dimethylacetamide and pyridine; and the reaction medium for the reaction with the electrophilic fluorination agent is acetonitrile in the presence of water.

12. A process according to claim 11, characterized by the fact that the reaction temperature for the reaction with benzoyl chloride is +80–85° C.; and the reaction temperature for the reaction with the electrophilic fluorination agent is −5±2° C.

13. A process according to claim 1, characterized by the fact that the deprotection in position C3 is carried out using an aqueous solution of metabisulfite and ammonia.

14. A process according to claim 1, characterized by the fact that the reaction medium for the reaction with benzoyl chloride is N,N'-dimethylacetamide and pyridine; and the reaction medium for the reaction with the electrophilic fluorination agent is acetonitrile in the presence of water.

15. A process according to claim 1, characterized by the fact that the reaction temperature for the reaction with benzoyl chloride is +80–85° C.; and the reaction temperature for the reaction with the electrophilic fluorination agent is −5±2° C.

16. A compound of the formula:

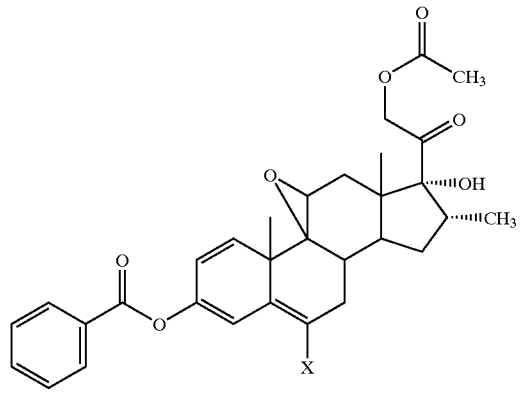

(III a)

wherein X is hydrogen or flurine.

17. A compound according to claim 16, characterized by the fact that X is hydrogen.

18. A compound according to claim 16, characterized by the fact that X is fluorine.

* * * * *

UNITED STATES PATENT AND TRADEMARK OFFICE
CERTIFICATE OF CORRECTION

PATENT NO. : 6,528,666 B1
DATED : March 24, 2003
INVENTOR(S) : Ivan Villax et al.

It is certified that error appears in the above-identified patent and that said Letters Patent is hereby corrected as shown below:

Title page,
Item [73], Assignee, "Horvione Limited (HK)" should read -- Hovione Limited (HK) --.

Column 5,
Line 10, "9,11α-" should read -- 9, 11β --.

Column 6,
Line 4, "20º C.±30º" should read -- 20º C. ± 3º --; and
Line 41, "...difluoro-17β, 7α-dihydroxy..." should read -- difluoro-11β, 17α-dihydroxy... --

Signed and Sealed this

Twelfth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,528,666 B1
DATED : March 24, 2003
INVENTOR(S) : Ivan Villax et al.

It is certified that error appears in the above-identified patent and that said Letters Patent is hereby corrected as shown below:

<u>Title page,</u>
Item [30], Foreign Application Priority Data, "Dec. 6, 2001   (PT)…………...102628"
should read -- June 12, 2001   (PT)……………..102628 --.

Signed and Sealed this

Eighth Day of March, 2005

JON W. DUDAS
*Director of the United States Patent and Trademark Office*

(12) INTER PARTES REEXAMINATION CERTIFICATE (0266th)
United States Patent
Villax et al.

(10) Number: US 6,528,666 C1
(45) Certificate Issued: May 31, 2011

(54) PROCESS OF PREPARATION OF FLUMETHASONE 21-ACETATE, OR FLUMETHASONE AND ITS 17-CARBOXYL ANDROSTEN ANALOGUE

(75) Inventors: Ivan Villax, Lisbon (PT); Zita Mendes, Lisbon (PT)

(73) Assignee: Hovione Limited, Wanchai (HK)

Reexamination Request:
No. 95/000,087, Apr. 5, 2005

Reexamination Certificate for:
Patent No.: 6,528,666
Issued: Mar. 4, 2003
Appl. No.: 10/162,862
Filed: Jun. 6, 2002

Certificate of Correction issued Aug. 12, 2003.

Certificate of Correction issued Mar. 8, 2005.

(30) Foreign Application Priority Data

Jun. 12, 2001 (PT) ................................. 102628

(51) Int. Cl.
*C07J 5/00* (2006.01)
*C07J 71/00* (2006.01)
*C07J 3/00* (2006.01)
*C07J 75/00* (2006.01)

(52) U.S. Cl. ....................................... 552/295; 549/544
(58) Field of Classification Search .................... 562/295
See application file for complete search history.

(56) References Cited

U.S. PATENT DOCUMENTS

| | | | |
|---|---|---|---|
| 3,499,016 A | 3/1970 | Lincoln et al. | 260/397.45 |
| 3,557,158 A | 1/1971 | Lincoln et al. | 260/397.45 |
| 3,817,978 A * | 6/1974 | Jenkins et al. | 536/4.1 |
| 4,188,322 A | 2/1980 | Castelli | |
| 4,255,331 A | 3/1981 | MacDonald | |
| 5,478,957 A | 12/1995 | Godard | |
| 6,528,666 B1 | 3/2003 | Villax | |
| 6,794,503 B2 * | 9/2004 | La Loggia et al. | 540/87 |

FOREIGN PATENT DOCUMENTS

| | | |
|---|---|---|
| JP | 60-6700 | 1/1985 |
| JP | 606700 A * | 1/1985 |

OTHER PUBLICATIONS

Lower SK. Chem 1 General Chemistry Reference Text. Introduction to acid–base chemistry. 1996, pp. 1–19.*
The Merck Index. Ninth Edition 1976, p. 8454.*
Pine SH. Organic Chemistry. Fifth Edition 1987, pp. 399–400.*
G. Sanker Lal. J. Org. Chem., 1993, 58:2791–2796.*
Response filed May 28, 2002 in application leading to U.S. Pat. No. 6,794,503.*
Response filed Dec. 15, 2003 in application leading to U.S. Pat. No. 6,794,503.*
Greene TW & Wuts PGM. Protective Groups in Organic Synthesis. Second Edition. 1991, pp. 100–101.*
Crossley, *The Relevance of Chirality to the Study of Biological Activity*, 48 Tetrahedron 8155, 8156, 8174, 8175 (1992).
Fried and Edwards, Organic Reactions in Steroid Chemistry, vol. I, (Van Nostrand Reinhold Co., 1972), 268–239, 324–327, 402–403.
Merck Index 10th Ed., (1996) p. 1472.
Bida et al., J. Nuclear Medicine, 1984, pp. 1327–1334, vol. 25—Issue 12, Society of Nuclear Medicine, US.
STN CA plus Database, Reg. No. 182202–347–5, Oct. 22, 1996 (STN).
International Search Report PCT/GB 02/02644.

* cited by examiner

*Primary Examiner*—Evelyn Huang

(57) ABSTRACT

A process for the preparation of high purity flumethasone in high yield involves C3 protecting 9,11β-epoxy-17α,21-dihydroxy-16α-methylpregna-1,4-diene-3,20-dione,21-acetate, fluorinating at 6α, removing the C3 protecting group, fluorinating the 9,11-epoxy group. The resulting flumethasone 21-acetate is treated with the methanolic potassium hydroxide in the presence of an oxidation agent, causing a simultaneous hydrolyzation and degradative oxidation, resulting in the formation of 6α,9α-difluoro-11β, 17α-dihydroxy-16α-methyl-17β-carboxy-androsta-1,4-diene-3-one in high yield. Flumethasone 21-acetate is alternatively hydrolyzed to yield flumethasone free alcohol.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

The patentability of claims 1-15 is confirmed.

Claims 16-18 are cancelled.

* * * * *